United States Patent
Neyens et al.

(10) Patent No.: US 11,959,813 B2
(45) Date of Patent: Apr. 16, 2024

(54) DEVICE AND METHOD FOR MEASURING A TEMPERATURE OF A MOLTEN METAL

(71) Applicant: HERAEUS ELECTRO-NITE INTERNATIONAL N.V., Houthalen (BE)

(72) Inventors: Guido Neyens, Houthalen (BE); Christiaan Radelet, Houthalen (BE); Marc Indeherberge, Houthalen (BE); Frank Stevens, Houthalen (BE)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 249 days.

(21) Appl. No.: 17/303,174

(22) Filed: May 21, 2021

(65) Prior Publication Data

US 2021/0396602 A1   Dec. 23, 2021

(30) Foreign Application Priority Data

Jun. 22, 2020 (EP) .................................... 20181481

(51) Int. Cl.
*G01K 13/00* (2021.01)
*G01K 13/02* (2021.01)
*C21C 5/52* (2006.01)

(52) U.S. Cl.
CPC .............. *G01K 13/026* (2021.01); *C21C 5/52* (2013.01); *C21C 2005/5288* (2013.01)

(58) Field of Classification Search
CPC ................... G01K 13/026; G21C 5/52; C21C 2005/5288
USPC ....................................................... 136/234
See application file for complete search history.

(56) References Cited

U.S. PATENT DOCUMENTS

| 4,444,516 A * | 4/1984 | Dostoomian | G01J 5/0875 385/12 |
| 4,697,463 A * | 10/1987 | Spooner | G01N 27/72 73/866 |
| 5,035,511 A * | 7/1991 | Berthold | G01K 11/32 250/227.12 |

(Continued)

FOREIGN PATENT DOCUMENTS

| CA | 2549084 A | * 11/2007 | |
| CA | 3116359 A1 | * 12/2021 | ........... G01K 13/026 |

(Continued)

OTHER PUBLICATIONS

17303174_2023-10-20_CA_3116359_A1_H.pdf, Dec. 2021.*
European Search Report issued in EP20181481.1 dated Nov. 13, 2020.

*Primary Examiner* — Gail Kaplan Verbitsky
(74) *Attorney, Agent, or Firm* — Blank Rome LLP

(57) ABSTRACT

A device for measuring a temperature of a molten metal bath, comprising:
  an optical cored wire;
  a tube, wherein the optical cored wire is at least partly arranged in the tube, wherein the tube has an outer diameter in the range of 4 mm to 8 mm, and a wall-thickness in the range of 0.2 mm to 0.5 mm; and
  a plurality of separating elements comprising more than two separating elements arranged in the tube spaced apart from each other, and forming at least one compartment between two of the more than two separating elements.

The invention also relates to a system and method for measuring a temperature of a molten metal bath.

20 Claims, 5 Drawing Sheets

(56) References Cited

U.S. PATENT DOCUMENTS

| | | | | |
|---|---|---|---|---|
| 5,447,373 A | * | 9/1995 | Okuhara | G01J 5/041 |
| | | | | 374/131 |
| 6,023,325 A | * | 2/2000 | Sahlgren | B23Q 17/0952 |
| | | | | 356/73.1 |
| 6,618,677 B1 | * | 9/2003 | Brown | G01F 1/74 |
| | | | | 73/152.33 |
| 6,769,805 B2 | * | 8/2004 | Williams | G01F 1/6884 |
| | | | | 374/166 |
| 7,384,192 B2 | * | 6/2008 | Dams | G01J 5/02 |
| | | | | 374/E13.013 |
| 7,748,896 B2 | * | 7/2010 | Dams | G01J 5/0821 |
| | | | | 374/208 |
| 9,541,665 B2 | * | 1/2017 | Shanks | E21B 47/113 |
| 2003/0197125 A1 | * | 10/2003 | De Saro | G01N 33/205 |
| | | | | 378/53 |
| 2007/0268477 A1 | | 11/2007 | Dams et al. | |
| 2009/0240455 A1 | * | 9/2009 | Fromme | G01K 11/32 |
| | | | | 702/85 |
| 2011/0280278 A1 | | 11/2011 | Cuypers et al. | |
| 2012/0147924 A1 | * | 6/2012 | Hall | G01K 11/3206 |
| | | | | 374/161 |
| 2015/0377710 A1 | | 12/2015 | Goda | |
| 2016/0168980 A1 | * | 6/2016 | Bedry | G01K 11/32 |
| | | | | 374/136 |
| 2021/0025759 A1 | * | 1/2021 | Lamp | G01J 5/0821 |

FOREIGN PATENT DOCUMENTS

| | | | | | |
|---|---|---|---|---|---|
| CN | 104568217 A | * | 4/2015 | | |
| CN | 109211412 A | | 1/2019 | | |
| EP | 1857792 A1 | | 11/2007 | | |
| EP | 2799824 A1 | | 11/2014 | | |
| EP | 2940441 A1 | * | 11/2015 | | F27D 11/08 |
| EP | 3156835 A1 | | 4/2017 | | |
| EP | 3290881 A1 | | 3/2018 | | |
| EP | 3339823 A1 | | 6/2018 | | |
| GB | 2543319 A | | 4/2017 | | |
| GB | 2558223 A | | 7/2018 | | |
| JP | 47007945 U | * | 9/1972 | | |
| JP | S4885676 U | | 10/1973 | | |
| JP | H07229791 A | | 8/1995 | | |
| JP | H0875553 A | | 3/1996 | | |
| JP | 62025225 A | * | 2/1997 | | |
| JP | H09159534 A | | 6/1997 | | |
| JP | 2000061594 A | | 2/2000 | | |
| JP | 2000186961 A | | 7/2000 | | |
| JP | 2010071666 A | | 4/2010 | | |
| KR | 20230025473 A | * | 3/2023 | | |

\* cited by examiner

DEVICE AND METHOD FOR MEASURING A TEMPERATURE OF A MOLTEN METAL

CROSS-REFERENCE TO RELATED APPLICATION

This application claims the benefit of European Application No. EP2018148.1 filed Jun. 22, 2020, the entire contents of which are incorporated herein by reference.

DESCRIPTION

The invention relates to a device for measuring a temperature of a molten metal bath comprising an optical cored wire and a tube. The invention also relates to a system and a method using a corresponding device for measuring the temperature of a molten metal bath.

There are several means and methods available for measuring the temperature of a molten metal bath in a metallurgical vessel during the metal making process. One of these means for measuring the temperature of the molten metal bath, particularly of iron or steel in a melting environment of an electric arc furnace (EAF), involves immersing an optical fiber surrounded by a metal tube into the molten metal. An optical fiber surrounded by a metal tube is often also referred to as optical cored wire. The optical fiber can receive thermal radiation and can convey the thermal radiation from the molten metal to a detector, e.g. a pyrometer. Suitable instrumentation can be associated with the detector for determining the temperature of the molten metal bath.

For measuring the temperature of the molten metal bath, the optical cored wire can be fed into the molten metal bath where it is consumed at an essentially constant rate for a continuous temperature measurement over a predetermined time interval. The leading tip of the optical cored wire is immersed into the metallurgical vessel, encountering on its way towards the molten metal bath first a hot atmosphere, followed by a slag layer and then the molten metal bath. Once the temperature measurement has been concluded, the tip of the optical cored wire can be partly retracted from the molten metal bath. The tip of the retracted optical cored wire is then the new leading tip for the next temperature measurement.

EP1857792A1 exemplarily describes a method and device for measuring a temperature of a molten metal bath using an optical cored wire.

Many of the devices known in the prior art are commonly constructed by using an optical fiber located in a tube. The gap between the optical wire and the metal tube is commonly filled with a filler material to protect the optical wire from the heat of the molten metal bath during the immersion. The optical cored wire and the tube can be fed into the molten metal bath with the same or different speeds to the same position in the molten metal bath.

Unfortunately, this construction does not always result in reliable measurements over the entire application range. Here, the term application range can be used to refer to the temperature range in which temperature measurements of the molten metal bath are conducted. Specifically, temperature measurements at the low temperature range in combination with the high slag temperatures can lead to high variances in the output data. For example, temperature ranges for normal steel grades are between 1520 and 1700° C. However, a majority of accordingly measured temperatures are commonly between 1550 and 1620° C.

Therefore, there is a need for a device and method with which more accurate temperature measurements are obtainable over the entire application range, while the consumption of the device in the molten metal is minimized.

The invention provides a device for measuring a temperature of a molten metal bath, comprising:
- an optical cored wire;
- a tube, wherein the optical cored wire is at least partly arranged in the tube, wherein the tube has an outer diameter in the range of 4 mm to 8 mm, and a wall-thickness in the range of 0.2 mm to 0.5 mm; and
- a plurality of separating elements comprising more than two separating elements arranged in the tube spaced apart from each other, and forming at least one compartment between two of the more than two separating elements.

Here, the term "optical cored wire" can be used to refer to an optical fiber that can be comprised in a casing, in particular a metal tube. The casing can fully encircle the optical fiber or can be at least partially open so that the casing is not fully encircling the optical fiber. Also, the casing can be at least partially filled with an agent for application in molten metal. Also, the optical fiber can be used without a casing.

The tube of the device can be a metal tube, in which the optical cored wire is extending along its length. For example, the optical cored wire can be arranged in the center of the metal tube and can extend into the direction of the metal tube.

According to the invention, the tube has:
- an outer diameter in the range of 4 mm to 8 mm, and
- a wall-thickness in the range of 0.2 mm to 0.5 mm.

The wall-thickness of the tube is preferably in the range of 0.3 mm to 0.4 mm. Also, tests in the molten metal bath have shown that the accuracy of the temperature measurements are linked to the mass of the cold material that is entering the molten metal bath during the temperature measurement. This mass per unit of time can depend on the feeding speed and the geometry of the device.

Also, the device comprises a plurality of separating elements comprising more than two separating elements arranged in the tube, and forming at least one compartment between two of the more than two separating elements.

Here, the term "compartment" relates to the volume between the different separating elements in the tube.

Here, the term "separating elements" relates to parts arranged inside the tube subdividing the volume within the tube.

The separating elements can be realized as disc-shaped elements that are arranged inside the tube comprising an opening, through which the optical cored wire is extending and which can at least partly support the optical cored wire. The opening is preferably in the middle of the elements to support the optical cored wire in the center of tube. However, in examples the separating elements can also have different shapes. For example, the separating elements can have a cubical, cylindrical, conical, triangular, spherical, pyramidal, trapezoidal and/or polygonal shape. In an example, the device comprises a plurality of separating elements comprising at least five separating elements arranged in the tube.

The separating elements can be attached to either one of the optical cored wire or the tube and can, advantageously, i.e. due to their arrangement between optical cored wire and tube minimize friction of the tube and the optical cored wire, and thus avoid stress. Further, when the device is being fed into the molten metal, the optical cored wire and the tube can move together. Hence, a relative movement of optical cored wire and tube can be minimized or even avoided when being fed into the molten metal bath.

The speed and the position of the optical cored wire and the tube can be essentially the same.

Advantageously, by employing separating elements to generate a compartment between at least any two separating elements the penetration of molten metal into the tube can efficiently be prevented.

Advantageously, by using a device as described above, the tube melts from the immersion end in a controlled way, which leads to more accurate temperature measurements. The actual temperature measurement can be conducted while the tube is melting in the molten metal bath.

By employing a device as described above, the tube advantageously does not melt before it enters into the molten metal bath. Also, the tube does not melt from the side, and molten metal penetrations to the inside of the tube can be minimized, which would adversely affect temperature measurements.

For example, a gas contained in the compartment will expand due to the temperature increase when the device is inserted into the molten metal bath. In an example, the pressure increase required to prevent steel ingress can be calculated by a simple calculation of the ferrostatic pressure at the targeted immersion depth in the molten metal bath.

Nevertheless, a sudden temperature rise of the molten metal bath temperature may generate a pressure build-up in these compartments in the order of around 6 bar. Such a pressure might cause cracks in the side wall of the tube before the melting process starts.

Further, it has been shown that minimizing the mass per unit of length by reducing the diameter and the wall-thickness of the tube, as defined above, contributes to obtaining more accurate temperature measurements. Also, for entering the molten metal bath without bending and floating, a minimum diameter is advantageous.

In an example, the tube comprises a material having a thermal conductivity higher than 30 W/mK at room temperature (RT).

Here, the term room temperature, RT can be used to refer to a temperature of about 20° C., in particular to a temperature in the range of 16° C. to 25° C.

In an example, a space between the optical cored wire and the tube is filled with:
  gas, a gas mixture, or
  a filler material comprising a low density material, in particular comprising a low density organic material.

The space can be, for example, filled with air or an inert gas. To minimize ingress of molten metal into the tube, which would lead to low output values, a filler material can be advantageously arranged at least partially in the space between the optical cored wire and the tube.

Here, the term "low density" can be used to refer to materials having a density of less than 2 g/cm$^3$, preferably less than 1 g/cm$^3$.

In an example, the filler material comprises cotton, wool, hemp, rice husks and/or flax. Other low density filler materials with an ash content less than 10% are also suitable.

The ash content can represent the incombustible component of a material remaining after the material has been completely burned.

In an example, the tube comprises a material or an alloy of at least one of the group of materials comprising: Iron, and/or alloyed steel grades.

Advantageously, the above mentioned materials have a thermal conductivity of higher than 30 W/mK at room temperature.

In an example, the product of thermal conductivity and wall-thickness of the tube is greater than 0.015 W/K.

A high heat conductivity in combination with a thin wall can be advantageous. The product of the wall thickness in mm and the heat conductivity can be advantageously higher than 0.015 W/K. In one example, the outer wall with a thickness of 0.3 mm requires a material with a heat conductivity>50 W/mK.

Advantageously, the higher the thermal conductivity of the material of the tube is chosen, the more homogeneous the temperature distribution during the heating of the tube will be. In contrast, an inhomogeneous temperature distribution may lead to uncontrolled blasting of the side walls of the tube resulting in unwanted ingress of the molten metal.

In a typical furnace, the distance between entry point and molten metal bath is in the range between 1-2 meters (m).

In an example, the separating elements are arranged in the tube spaced apart from each other at a distance which is smaller than the distance from the entry point in the furnace to a height of the molten metal bath. In this example, the separating elements can be arranged to form a ventilation path over the length of the device.

In one example, the separating elements comprise a silicone, preferably a two-component silicone material, a rubber material, a leather material, a cork material, and/or a metal material.

To overcome the adverse effects of a sudden pressure build-up, small compartments can be chosen, which implies that during a measurement at least one compartment is fed into the furnace. The gases in this compartment will expand and pressure will build-up due to thermal expansion. Advantageously, the ventilation path prevents steel and slag ingress from the side wall of the tube. During the immersion of the device, expanding gas can partly evacuate through the immersion end of the device.

In an alternative example, the separating elements are arranged in the tube spaced from each other at a distance which is larger than the distance from an entry point in the furnace to the height of the molten metal bath.

In this case, the next compartment is partly arranged within the furnace and outside the furnace. Advantageously, this can prevent the heating of the gases over the total compartment length and as such reduce the maximum pressure obtained in the compartment to overcome the adverse effects of a sudden pressure build-up. Also, in the before mentioned example, the separating elements can be arranged in the tube in a gas-tight manner to provide a seal between the optical cored wire and the inside of the tube.

In another example, the separating elements are arranged in the tube spaced apart from each other at a distance in the range of 2 m to 5 m, preferably at a distance of 3 to 4 m. In most metallurgical processes, the molten metal bath is covered by a slag layer with a lower density than the molten metal bath. For example, in a steel making processes, the density of the molten steel is around 7 g/cm$^3$ with a slag cover with a density around 2 g/cm$^3$. During the processing stages in converter, electric arc and ladle furnaces this density can drop further due to the slag foaming caused by $CO/CO_2$ bubbles. In case the device has a density higher than the bath, it will tend to sink to the bottom, with a lower density it will show a tendency to float.

In one example, the device comprises a density in the range of 0.8 g/cm$^3$ to 4 g/cm$^3$, in particular in the range of 1 g/cm$^3$ to 3 g/cm$^3$.

To prevent the risk of flotation during immersion of the device, a material density in the range of 0.8 g/cm³ to 4 g/cm³, in particular in the range of 1 g/cm³ to 3 g/cm³, is advantageous.

An electric arc furnace process will have a very broad density range for the slag. With an estimated slag thickness of around 30 cm in a collapsed phase, the slag thickness can rise to the furnace roof while foaming. Thus, a device used in this process needs to be applicable in this range to allow obtaining accurate temperature measurements.

The invention also relates to a system, comprising a device as described herein; and feeding means for feeding a leading tip of the device in a molten metal bath. The system may also further comprise a furnace having an entry point for the device and holding the molten metal bath and slag cover.

The invention further relates to a method for measuring the temperature of a molten metal bath, using a device or a system as described herein, comprising:

feeding the device for measuring the temperature with a leading tip directed towards the molten metal with a feeding rate in the range of 10 g/s to 50 g/s into the molten metal bath; and measuring the temperature of the molten metal.

A feeding rate of 50 g/s might be considered as maximum. In applications with high temperatures this speed needs to be applied to reach sufficient depth in the molten metal bath. In applications with low temperatures this value may be lower. In all steelmaking applications a minimum of 10 g/s is required to obtain a minimum immersion depth.

For example, in electric arc furnace applications most accurate measurements can be obtained with a feeding rate of around 30 g/s, in ladle furnace applications with a feeding rate of around 20 g/s and in ladle applications with a feeding rate of around 16 g/s.

As already described above, the accuracy of the temperature measurements can be seen to be linked to the mass of the cold material that is entering the molten metal bath during the temperature measurement. This mass per unit of time can depend on the feeding speed and the geometry of the device.

Advantageously, by feeding a device as described above with the feeding speeds as defined in the method more accurate temperature measurements can be obtained.

In an example, the optical cored wire and the tube are fed together at the same speed into the molten metal bath.

In the following two advantageous examples are described:

In a first example the required feeding rate to obtain an accurate temperature measurement was verified. A device comprising an optical cored wire and a low carbon steel tube with an outer diameter of 6 mm and a wall-thickness of 0.3 mm, having a density around 1.6 g/cm³ can be fed in the molten metal bath at a speed of 800 mm/s to a depth of 300 mm. A density around 1.6 g/cm³ corresponds to a mass of 44.1 g/m. At this speed the measurement will be accurate over the total application range. Advantageously, the chosen configuration will remain in the molten-metal and will float towards the direction of the molten metal-slag-interface.

The following example parameters were obtained in regard to the first example:

Time=300 mm/800 mm/s=0.375 s

Mass=44.1 g/m*0.3 m=13.2 g

Mass/time=13.2 g/0.375 s=35.2 g/s

In a second example the maximum feeding speed to obtain an accurate temperature measurement was determined. A device having a density around 2.2 g/cm³ (corresponding to 68.6 g/m) with a low carbon steel tube with an outer diameter of 7 mm and a wall-thickness of 0.4 mm, can be fed in the molten metal bath to a depth of 400 mm with a maximum speed of 728 mm/s. Up to this speed the measurement will be reliable over the total application range. The chosen configuration will remain in the molten-metal, and will float towards the direction of the molten metal-slag-interface.

The following examples parameters were obtained in regard to the second example:

Mass=68.6 g/m*0.4 m=27.4 g

Time=27.4 g/50 g/s=0.54 s

Speed=400 mm/0.54 s=728 mm/s.

The idea underlying the invention shall subsequently be described in more detail with respect to the embodiments shown in the figures. Herein:

FIG. 1 shows a schematic view of a system for measuring a temperature of a molten metal bath 15 according to an embodiment of the invention.

Figure 1:
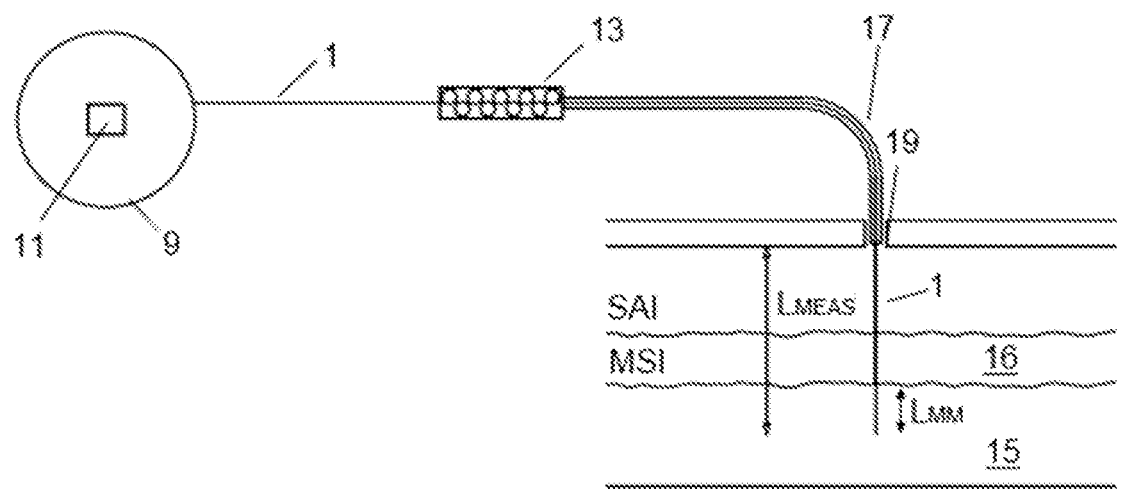
FIG. 1 shows a schematic view of a system for measuring a temperature of a molten metal bath according to an embodiment of the invention.

As shown in FIG. 1, the system comprises a device 1 which is located at least partly on a coil 9 and is at least in part unwound from the coil 9 for conducting a measurement. A first end of the device 1 is connected to a pyrometer 11 which in turn could be connected to a computer system (not shown) to process the data obtained with the device 1. As shown in FIG. 1, the device 1 is fed by means of a feeder 13 through a guide tube 17 in a vessel having an entry point 19 and containing the molten metal bath 15. The temperature of a part of the device 1 extending from the coil 9 to the entry point 19 can be considered to be low, which could be a temperature ranging from room-temperature up to 100° C. Once passing the entry point 19 in the direction of the molten metal bath 15, a hot atmosphere of up to 1700° C. or even higher is first encountered, followed by a slag layer 16 which is in turn followed by the molten metal bath 15. The entry point 19 to the vessel could be equipped with a blowing lance (not shown in FIG. 1) to prevent metal and slag-penetration into the device 1. The leading tip of the device 1 submerged into the molten metal bath 15 will melt and during this melting stage the temperature measurement can be obtained. The distance covered by the leading tip of the device 1 inside the molten metal 15 is indicated by $L_{MM}$. After the measurement is taken, the part of the device 1 located in the hot atmosphere and extending through the slag layer 16 can be fed back into the direction of the coil 9 and can be reused for the next measurement. The distance covered by the leading tip of the device 1 inside the vessel is indicated by $L_{MEAS}$ in FIG. 1. Also shown in FIG. 1 are the Slag Layer—Atmosphere Interface, SAI, and the Molten Metal—Slag Layer Interface, MSI.

Figure 2:
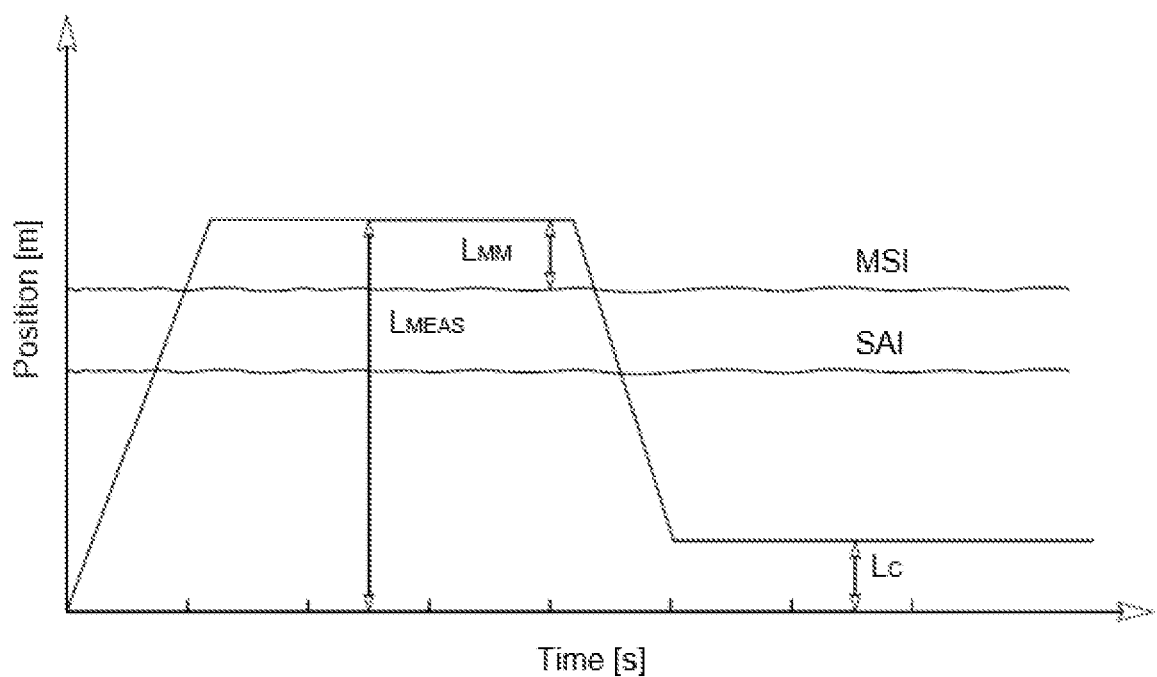
FIG. 2 shows a schematic position-time graph indicating the immersion of a leading tip of the device, before, during and after measuring the temperature of the molten metal.

FIG. 2 shows a schematic of a position-time graph indicating the immersion of the leading tip of the device, before, during and after measuring the temperature of the molten metal. For the sake of the present explanation, the position-time graph of FIG. 2 shows a simplified case, where it is assumed that the leading tip of the device is not melting during the measurement. The entry point which is shown in FIG. 1 is considered to be the entry point of the vessel and a point of reference for the measurement. The distance covered inside the vessel $L_{MEAS}$ is shown in FIG. 2 as well as the distance covered by the leading tip inside the molten metal $L_{MM}$ and the length of the device that is typically consumed for taking one temperature measurement $L_C$. The sequence will end with a new leading tip of the device positioned at the entry point of the vessel. The length of the device $L_{MM}$ immersed in the molten metal bath 15 and the feedforward distance is reduced with the length in the molten metal bath to obtain the return distance.

Figure 3A:
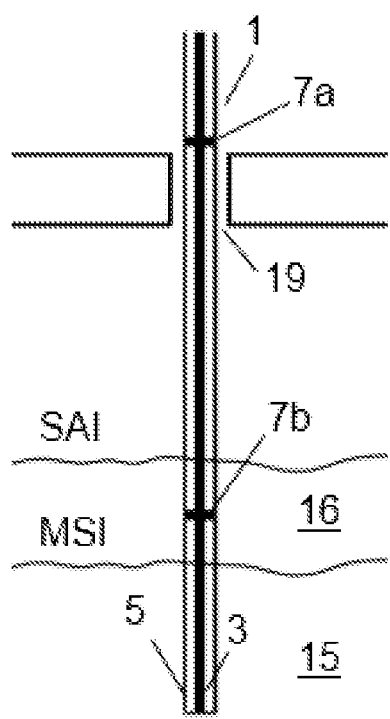
FIGS. 3A, 3B show schematic views of devices according to a first embodiment and a second embodiment of the invention.
Figure 3B:
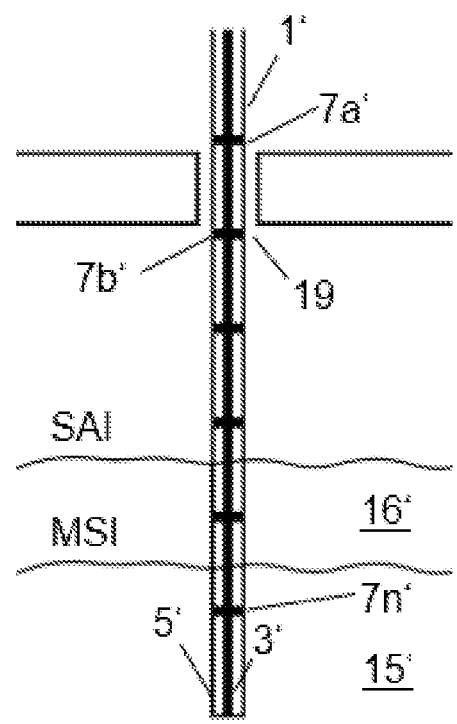

FIGS. 3A and 3B show schematic views of devices 1, 1' according to a first embodiment and a second embodiment of the invention during a measurement sequence. FIGS. 3A and 3B show a part of the device that is fed from the entry point 19 in the molten metal bath 15.

In both embodiments the devices 1, 1' comprise more than two separating elements 7a, 7a', 7b, 7b', 7n' arranged in the tube 5, 5' which form at least one compartment between two of the separating elements 7a, 7a', 7b, 7b', 7n'.

FIG. 3A shows a device 1 according to a first embodiment having a configuration with large compartments. For the configuration according to the first embodiment, the separating elements 7a, 7b are arranged in the tube 5 around the optical cored wire 3 spaced from each other at a distance which is larger than the distance from the entry point 19 to the Molten Metal—Slag Layer Interface, MSI. In the shown configuration, the length of the compartment is chosen in such a way that no closed compartment is positioned in the vessel over its entire length. In case the entry point 19 is equipped with a blowing lance (not shown), a small part inside the vessel can be considered as cold. As shown in FIG. 3A the compartment is formed between two separating elements 7a, 7b with a first separating element 7a in a cold area, and an opposite second separating element 7b in a hot area.

FIG. 3B shows a device 1' according to a second embodiment having a configuration with small compartments. Here, the separating elements 7a', 7b', 7n' are arranged in the tube 5' spaced from each other at a distance which is smaller than the distance from the entry point 19 in the furnace to the Molten Metal—Slag Layer Interface, MSI. In the embodiment that is shown in FIG. 3B the separating elements 7a', 7b', 7n' are at least partly gas permeable for forming a ventilation path from the immersion end into the direction of the coil (not shown in FIG. 3B).

Figure 4:
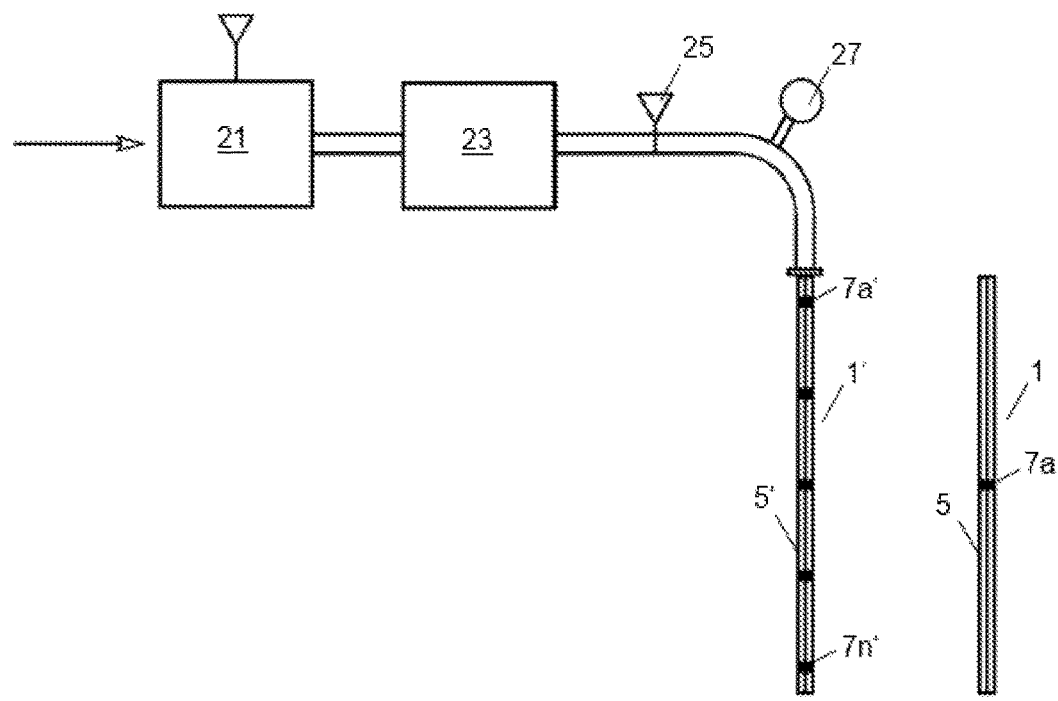
FIG. 4 shows a schematic view of a system for verifying the gas-tightness of the compartments according to embodiments of the invention.

FIG. 4 shows a schematic view of a system for verifying the gas-tightness of the compartments formed by the separating elements 7a, 7b, 7a', 7n' arranged in the tubes 5, 5', of the devices 1, 1' shown in FIGS. 3A and 3B.

The shown system for verifying the gas-tightness comprises a pressure regulator 21, a flowmeter 23, a valve 25 and a pressure meter 27. For testing, either one of the shown devices 1, 1' can be connected to the system. However, the skilled person would know that there are also alternative means available for verifying the gas-tightness of the compartments.

To obtain accurate measurements at least the compartments of the device 1 having the configuration with large compartments should be gastight. The "gas-tightness" of the compartments can be tested by testing the gas-tightness of the individual separating elements 7a, 7a', 7n' to show a counter-pressure of at 0.8 bar. As a rule of thumb, it can be said that the longer the length of the compartment, the higher this pressure should be. It has been shown that chamber lengths up to the double length of the length in the hot zone show favorable results with a counter-pressure above 0.9 bar. Separating elements with organic compounds may cause gas formation in the hot zone. These separating elements may burn during the measurement sequence and create a ventilation path. Device 1' which is shown in FIG. 4 as connected to the system, may show a counter-pressure of 0.2 to 0.8 bar based on testing a device 1' comprising 20 separating elements. Device 1 which is shown in FIG. 4 next to device 1', may show a counter pressure of >0.9 bar based on a test with a device 1 comprising a single separating element.

As an example, a method for verifying the gas-tightness using the system shown in FIG. 4 is described below with the subsequent steps:
1. Set pressure regulator 21 to 1 bar overpressure with valve 25 closed;
2. Open valve 25 and set flow meter 23 to 5 l/min;
3. Connect specimen 1, 1' to the system; and
4. Measure pressure on the pressure meter 27.

Figure 5A:
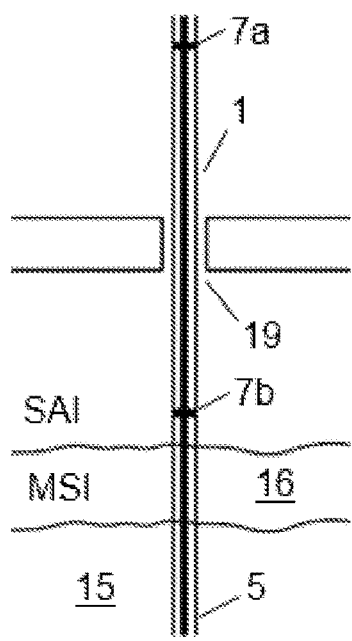
FIGS. 5A-5C show schematic views of immersing a device according to a first embodiment of the invention into a molten metal bath.
Figure 5B:
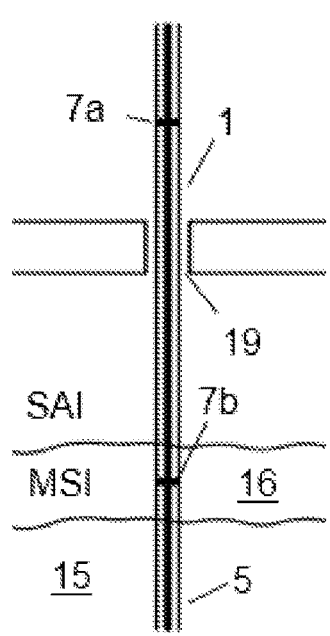
Figure 5C:
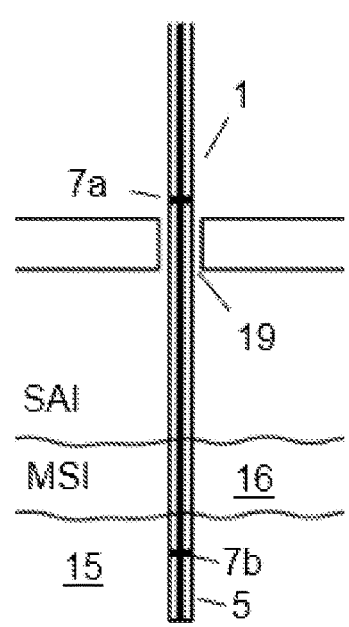

FIGS. 5A-5C show schematic views of a device 1 according to the first embodiment. In particular, FIGS. 5A-5C show a part of the device 1 that is fed from the entry point 19 in the molten metal bath 15. From the left hand side to the right hand side three stages of immersing the device 1 into the molten metal bath 15 are exemplarily shown in the figures.

In FIG. 5A it is shown that a separating element 7b is positioned in the hot atmosphere. Metal and slag penetration into the leading tip of the device 1 can be prevented by means of the separating element 7b. High pressure in the tube 5 can be prevented, because the leading tip can ventilate into the molten metal bath 15 and the next compartment is arranged partly in the cold zone. After the measurement sequence the part of the cored wire in the molten metal bath 15 will be molten and with the next measuring sequence the new leading tip of the device 1 will be positioned as shown in FIG. 5B. Again, metal and slag penetration are avoided by the separating element 7b and overpressure in the next compartment is reduced since the compartment is partly arranged in the cold area. After the sequence shown in FIG. 5B is concluded, the new leading tip will be positioned as shown in FIG. 5C. During this measurement sequence the separating element 7b will enter the molten metal bath 15 and the tube 5 will melt before the internal pressure in the compartment will become too high. After the sequence shown in FIG. 5C is concluded, the next measurement will again resemble the sequence shown in FIG. 5A.

Figure 6A:
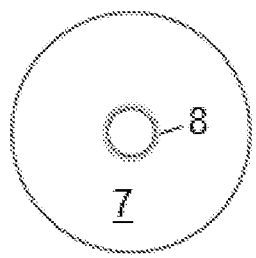
FIGS. 6A-6C show schematic views of different configurations of separating elements according to embodiments of the invention.
Figure 6B:
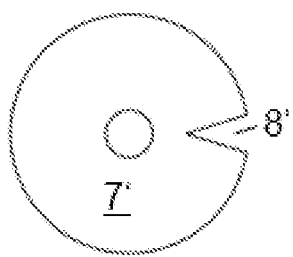
Figure 6C:
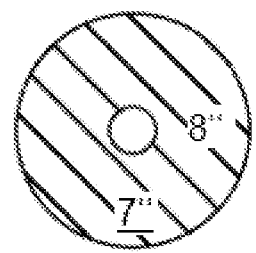

FIGS. 6A-6C show schematic views of different configurations of separating elements 7, 7', 7" according to embodiments of the invention. The skilled person would know that in examples described herein, different configurations can be used together inside a tube.

In FIG. 6A a separating element 7 is shown which is gas permeable and which has a ventilation path 8 arranged around a central opening for the optical cored wire (not shown in FIG. 6A). The shown configuration allows relative movement of the optical cored wire during the bending and straightening of the device during the feeding sequence.

In FIG. 6B a separating element 7' is shown which is gas permeable and which has a ventilation path 8' arranged in the surface of the separating element 7', where the separating element 7' is in contact with the tube of the device when installed inside the tube.

In FIG. 6C a separating element 7" is shown which is gas-permeable, wherein the ventilation path 8" is created by choosing a material being gas permeable.

Figure 7A:
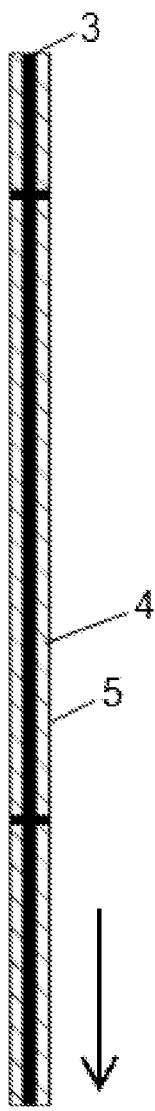
FIGS. 7A-7C show schematic views of devices according to embodiments of the invention.
Figure 7B:
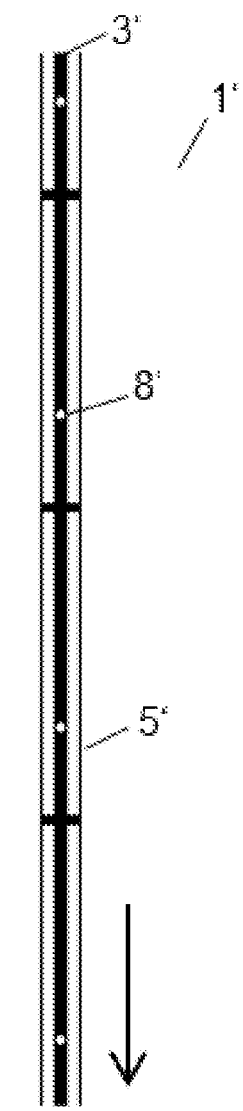
Figure 7C:
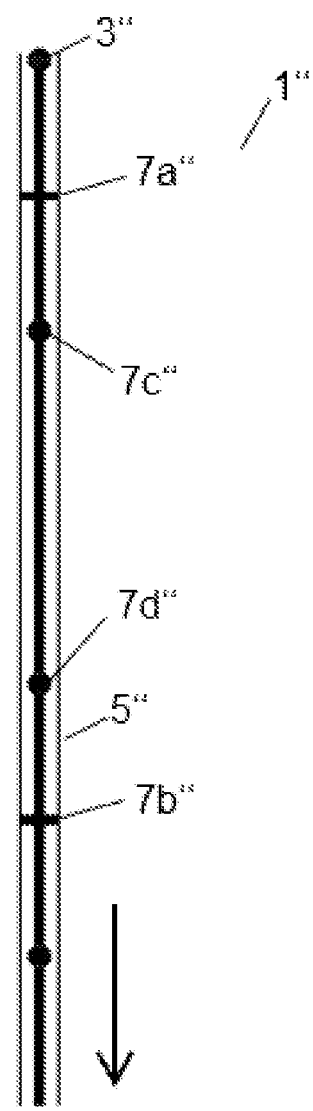

FIGS. 7A-7C show schematic views of devices 1, 1', 1" according to embodiments of the invention. An arrow in each one of the figures indicates the immersion direction of the devices 1, 1', 1" into the molten metal bath (not shown in FIGS. 7A-7C).

FIG. 7A shows a device 1 having a filler material 4 arranged in the space between the tube 5 and the optical cored wire 3. The filler material 4 could be a material having a low density such as cotton.

FIG. 7B shows a device 1', whereby the ventilation path 8' is created by means of apertures arranged in the outer diameter of the optical cored wire 3'.

FIG. 7C shows a device 1" having separating elements 7a", 7b" that can provide a gas-tight seal and additional separating elements 7c", 7d" arranged between separating elements 7a", 7b" that are not in direct contact with the tube 5".

LIST OF REFERENCE NUMERALS 1, 1', 1" Device
3, 3', 3" Optical Cored Wire
4 Filler Material
5, 5', 5" Tube
7-7", 7a-7n" Separating Elements
8, 8', 8" Ventilation Path
9 Coil
11 Pyrometer
13 Feeder
15, 15' Molten Metal Bath
16, 16' Slag Layer
17 Guide Tube
19 Entry Point
21 Pressure Regulator
23 Flow meter
25 Valve
27 Pressure Meter
SAI Slag Layer—Atmosphere Interface
MSI Molten Metal—Slag Layer Interface
$L_{MEAS}$ Measurement Distance
$L_{MM}$ Distance in Molten Metal
$L_C$ Length of Device Consumed in Molten Metal

The invention claimed is:

1. A device for measuring a temperature of a molten metal bath, comprising:
an optical cored wire comprising an optical fiber at least partially surrounded by a first tube made of a metal;
a second tube, wherein the optical cored wire is at least partly arranged in the second tube, wherein the second tube has an outer diameter in the range of 4 mm to 8 mm, and a wall-thickness in the range of 0.2 mm to 0.5 mm; and
a plurality of separating elements arranged between the optical cored wire and the second tube, wherein
each of the plurality of separating elements are at least partly gas permeable to allow for the movement of gases therethrough,
adjacent separating elements of the plurality of separating elements are spaced apart from each other, and
each of the plurality of separating elements are attached to the optical cored wire or the second tube,
spaces between the optical cored wire, the second tube and adjacent separating elements of the plurality of separating elements are filled with a filler consisting of a gas or a gas mixture, and
the optical fiber is configured to receive thermal radiation from a molten metal bath and convey the thermal radiation to a detector.

2. The device of claim 1, wherein the second tube comprises a material having a thermal conductivity higher than 30 W/mK at room temperature.

3. The device of claim 2, wherein the product of thermal conductivity and wall-thickness of the second tube is greater than 0.015 W/K.

4. The device of claim 1, wherein the second tube comprises a material or an alloy of at least one of iron and an alloyed steel grade.

5. The device of claim 1, wherein adjacent separating elements are arranged in the second tube spaced apart from each other at a distance which is smaller than the distance from an entry point in a furnace to a height of the molten metal bath.

6. The device of claim 1, wherein adjacent separating elements are arranged in the second tube spaced apart from each other at a distance which is larger than the distance from an entry point in a furnace to the height of the molten metal bath.

7. The device of claim 1, wherein the separating elements are arranged in the second tube such that adjacent separating elements are spaced apart from each other at a distance in the range of 2 meters (m) to 5 m.

8. The device of claim 1, wherein the separating elements comprise a silicone material, a rubber material, a leather material, a cork material, and/or a metal material.

9. The device of claim 1, wherein the device has a density in the range of 0.8 g/cm³ to 4 g/cm³.

10. A system, comprising:
a device according to claim 1; and
feeding means for feeding a leading tip of the device in a molten metal bath.

11. A method for measuring the temperature of a molten metal bath, using a device according to claim 1, comprising:
feeding the device for measuring the temperature with a leading tip directed towards the molten metal with a feeding rate in the range of 10 g/s to 50 g/s into the molten metal bath; and
measuring the temperature of the molten metal.

12. A method for measuring the temperature of a molten metal bath, using a system according to claim 10, comprising:
feeding the device for measuring the temperature with a leading tip directed towards the molten metal with a feeding rate in the range of 10 g/s to 50 g/s into the molten metal bath; and
measuring the temperature of the molten metal.

13. The device of claim 1, wherein the separating elements are arranged in the second tube such that adjacent separating elements are spaced apart from each other at a distance in the range of 3 m to 4 m.

14. The device of claim 1, wherein the device has a density in the range of 1 g/cm$^3$ to 3 g/cm$^3$.

15. The device of claim 1, wherein each of the plurality of separating elements are attached to the optical cored wire.

16. The device of claim 1, wherein each of the plurality of separating elements are attached to the second tube.

17. The device of claim 1, wherein the wall-thickness of the second tube is in the range of 0.3 mm to 0.4 mm.

18. The device of claim 1, wherein the gas is air.

19. The device of claim 1, wherein the gas is an inert gas.

20. A device for measuring a temperature of a molten metal bath, comprising:
- an optical cored wire comprising an optical fiber at least partially surrounded by a first tube made of a metal;
- a second tube, wherein the optical cored wire is at least partly arranged in the second tube, wherein the second tube has an outer diameter in the range of 4 mm to 8 mm, and a wall-thickness in the range of 0.2 mm to 0.5 mm; and
- a plurality of separating elements arranged between the optical cored wire and the second tube, wherein
  - each of the plurality of separating elements are at least partly gas permeable to allow for the movement of gases therethrough,
  - adjacent separating elements of the plurality of separating elements are spaced apart from each other, and
  - the optical fiber is configured to receive thermal radiation from a molten metal bath and convey the thermal radiation to a detector.

\* \* \* \* \*